(12) United States Patent
Allouche et al.

(10) Patent No.: US 11,391,122 B2
(45) Date of Patent: Jul. 19, 2022

(54) MODULAR WELL TESTING SYSTEMS AND METHODS

(71) Applicant: Schlumberger Technology Corporation, Sugar Land, TX (US)

(72) Inventors: Francis Dominique Allouche, Clamart (FR); Mathilde Jan, Paris (FR); Ibrahim El Alami, Clamart (FR); Pierre Chaigne, Clamart (FR); Mahesh Shenoy, Houston, TX (US); Gilbert Conort, Paris (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 851 days.

(21) Appl. No.: 16/310,954

(22) PCT Filed: Oct. 3, 2016

(86) PCT No.: PCT/US2016/055091
§ 371 (c)(1),
(2) Date: Dec. 18, 2018

(87) PCT Pub. No.: WO2018/004714
PCT Pub. Date: Jan. 4, 2018

(65) Prior Publication Data
US 2020/0308962 A1 Oct. 1, 2020

(30) Foreign Application Priority Data

Jun. 28, 2016 (EP) ..................................... 16290118

(51) Int. Cl.
*E21B 43/00* (2006.01)
*E21B 43/34* (2006.01)
(Continued)

(52) U.S. Cl.
CPC .............. *E21B 43/00* (2013.01); *E21B 21/06* (2013.01); *E21B 43/34* (2013.01); *G01N 1/14* (2013.01); *G01N 33/2823* (2013.01)

(58) Field of Classification Search
CPC ...... E21B 43/00; E21B 43/34; E21B 43/2607; E21B 21/06; G01N 33/2823
See application file for complete search history.

(56) References Cited

U.S. PATENT DOCUMENTS 4,352,739 A * 10/1982 Oliver, Jr. .............. B01D 21/00
210/739
4,522,258 A * 6/1985 DeWald ................. E21B 33/03
166/57
(Continued)

FOREIGN PATENT DOCUMENTS

CN 204252961 U 4/2015
KR 20140012431 A * 2/2014
(Continued)

OTHER PUBLICATIONS

International Search Report and Written Opinion issued in the related PCT Application PCT/US2016/055091, dated Feb. 27, 2017 (15 pages).
(Continued)

*Primary Examiner* — Jennifer H Gay
(74) *Attorney, Agent, or Firm* — Trevor G. Grove

(57) ABSTRACT

A well testing apparatus includes tank manifold skids connected to tanks, a pump manifold skid, and a control system. Each tank manifold skid includes first pipework, second pipework, and valves. The first pipework of each tank manifold skid cooperates with the first pipework of another tank manifold skid to enable fluid communication between the tank manifold skids. The second pipework of each tank manifold skid enables fluid communication between the first pipework and a connected tank, while the valves can control (Continued)

flow through the second pipework to the tank. The pump manifold skid is coupled to the tank manifold skids and includes fluid manifolds, pumps, and valves. The control system includes a control unit for remotely actuating the valves to selectively control fluid flow from a separator to the tanks via the pump manifold skid and the tank manifold skids. Additional systems, methods, and devices are also disclosed.

9 Claims, 12 Drawing Sheets

(51) Int. Cl.
*G01N 33/28* (2006.01)
*E21B 21/06* (2006.01)
*G01N 1/14* (2006.01)

(56) References Cited

U.S. PATENT DOCUMENTS

| | | | | |
|---|---|---|---|---|
| 4,597,437 | A * | 7/1986 | McNabb | E21B 43/34 |
| | | | | 166/79.1 |
| 4,819,955 | A * | 4/1989 | Cobb | B60P 3/22 |
| | | | | 220/1.5 |
| 9,803,459 | B1 * | 10/2017 | Leal | B01D 21/2405 |
| 10,605,075 | B2 * | 3/2020 | Suheil | E21B 43/12 |
| 11,035,840 | B2 * | 6/2021 | Miglis | B01D 19/0042 |
| 2007/0151907 | A1 * | 7/2007 | Duhe | C02F 1/34 |
| | | | | 210/170.01 |
| 2009/0107218 | A1 * | 4/2009 | Latham | G01N 1/14 |
| | | | | 73/61.44 |
| 2009/0321080 | A1 * | 12/2009 | Breivik | E21B 43/40 |
| | | | | 166/345 |
| 2013/0068007 | A1 * | 3/2013 | Carelli | E21B 43/34 |
| | | | | 73/152.29 |
| 2013/0248182 | A1 * | 9/2013 | Chong | E21B 21/062 |
| | | | | 166/285 |
| 2014/0020775 | A1 * | 1/2014 | Iboldi | E21B 43/34 |
| | | | | 137/565.17 |
| 2014/0096836 | A1 * | 4/2014 | Romero Maimone | E21B 43/12 |
| | | | | 137/10 |
| 2014/0137643 | A1 * | 5/2014 | Henry | G01F 1/78 |
| | | | | 73/152.31 |
| 2014/0251623 | A1 * | 9/2014 | Lestz | E21B 43/267 |
| | | | | 166/308.2 |
| 2015/0001161 | A1 * | 1/2015 | Wiemers | B01D 17/047 |
| | | | | 210/739 |
| 2017/0122097 | A1 * | 5/2017 | Suheil | E21B 47/10 |
| 2021/0102451 | A1 * | 4/2021 | Robinson | E21B 43/2607 |
| 2021/0148385 | A1 * | 5/2021 | Brunty | E21B 43/2607 |

FOREIGN PATENT DOCUMENTS

| | | | | |
|---|---|---|---|---|
| WO | WO-2004085789 A2 * | 10/2004 | | E21B 43/017 |
| WO | WO-2010080867 A2 * | 7/2010 | | E21B 21/06 |
| WO | 2010151661 A2 | 12/2010 | | |
| WO | WO-2011036556 A2 * | 3/2011 | | F17D 1/08 |
| WO | WO-2014028317 A1 * | 2/2014 | | E21B 43/267 |
| WO | WO-2018004713 A1 * | 1/2018 | | B01D 17/0211 |

OTHER PUBLICATIONS

International Preliminary Report on Patentability issued in the related PCT Application PCT/US2016/055091, dated Jan. 10, 2019 (11 pages).
Office action issued in the CN Application 201680087774.X dated Oct. 23, 2020 (18 pages).
Office Action issued in the EP Application 16781639.6, dated May 8, 2020 (7 pages).

* cited by examiner

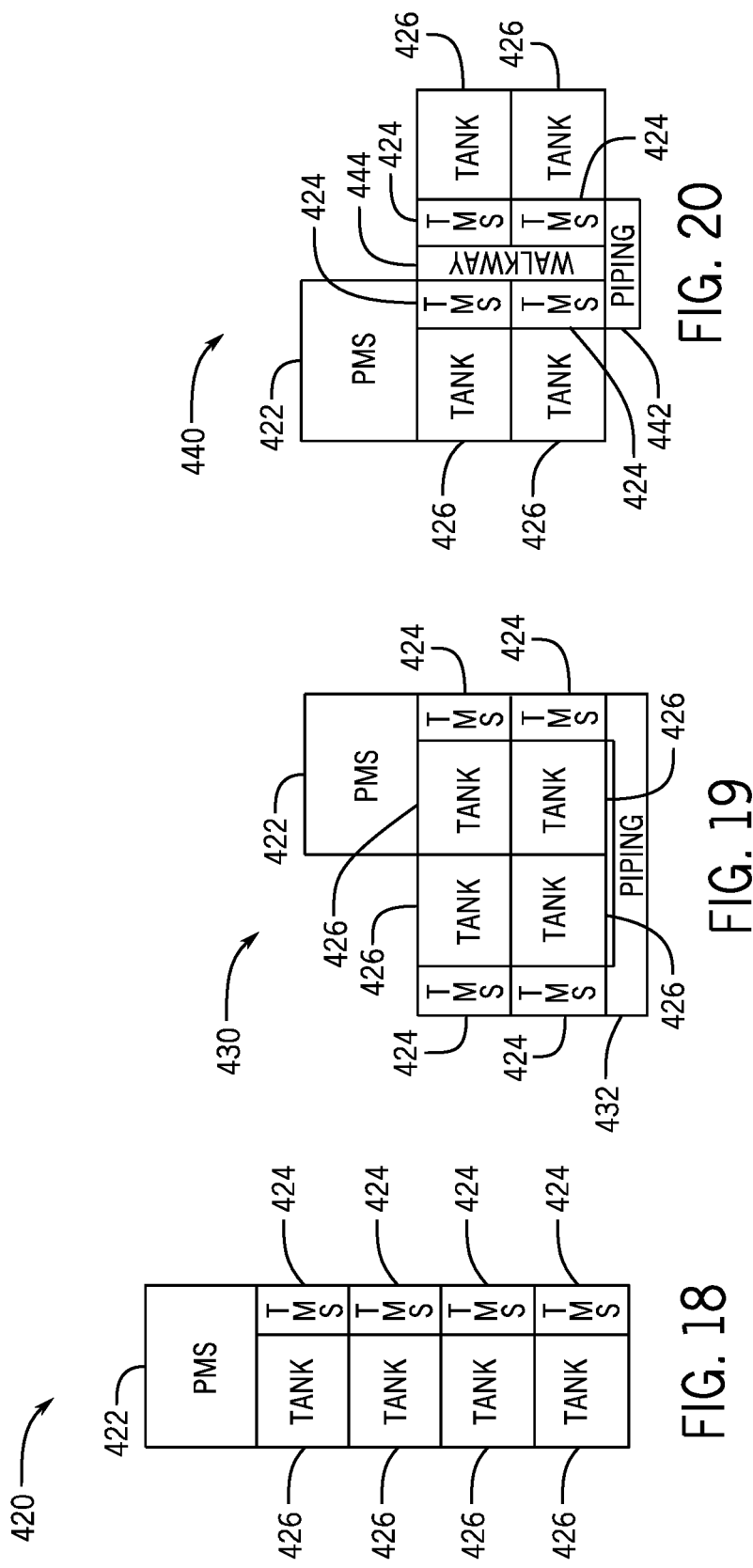

MODULAR WELL TESTING SYSTEMS AND METHODS

BACKGROUND

Field

This disclosure relates to well testing systems, apparatuses, devices, and methods for executing a well test.

Description of the Related Art

Wells are generally drilled into subsurface rocks to access fluids, such as hydrocarbons, stored in subterranean formations. The subterranean fluids can be produced from these wells through known techniques. Operators may want to know certain characteristics of produced fluids to facilitate efficient and economic exploration and production. For example, operators may want to know flow rates of produced fluids. These produced fluids are often multiphase fluids (e.g., those having some combination of water, oil, and gas), making measurement of the flow rates more complex. Surface well testing provides various information about the reservoir and its fluids, such as volumetric flow rates of fluids produced from a well and properties of the produced fluids. Surface well testing equipment may be temporarily installed at a wellsite for well test operations and then removed at the conclusion of testing.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

Some embodiments of the present disclosure relate to a well testing apparatus. In one embodiment, a well testing apparatus includes tank manifold skids connected to tanks, a pump manifold skid, and a control system. Each tank manifold skid includes a platform with first pipework, second pipework, and valves. The first pipework of each tank manifold skid cooperates with the first pipework of another tank manifold skid to enable fluid communication between the tank manifold skids. The second pipework of each tank manifold skid enables fluid communication between the first pipework and a connected tank, while the valves can control flow through the second pipework to the tank. The pump manifold skid is coupled to the tank manifold skids and includes an additional platform with fluid manifolds, fluid transfer pumps, and valves for controlling flow of fluids between the tank manifold skids and the fluid manifolds on the additional platform. The control system includes the valves of the platform, the valves of the additional platform, and a control unit for remotely actuating the valves to selectively control fluid flow from a separator to the tanks via the pump manifold skid and the tank manifold skids.

In another embodiment, a method includes assembling a modular portion of a well testing apparatus at a non-wellsite location. Assembling the modular portion can include coupling a first surge tank to a first tank manifold skid, coupling a second surge tank to a second tank manifold skid, and coupling the first tank manifold skid to the second tank manifold skid. The method can also include transporting the assembled modular portion as a single unit from the non-wellsite location at which the modular portion was assembled to a wellsite and connecting the assembled modular portion to additional components at the wellsite to facilitate well testing via the well testing apparatus including the modular portion.

In a further embodiment, a well testing apparatus includes a separator and fluid tank modules each having a single fluid tank connected to a single tank manifold skid. The well testing apparatus can also include a pump manifold module coupled to the separator and to each of the fluid tank modules such that each of the fluid tanks of the fluid tank modules is coupled to the separator via its own single tank manifold skid and the pump manifold module.

Various refinements of the features noted above may exist in relation to various aspects of the present embodiments. Further features may also be incorporated in these various aspects as well. These refinements and additional features may exist individually or in any combination. For instance, various features discussed below in relation to the illustrated embodiments may be incorporated into any of the above-described aspects of the present disclosure alone or in any combination. Again, the brief summary presented above is intended just to familiarize the reader with certain aspects and contexts of some embodiments without limitation to the claimed subject matter.

BRIEF DESCRIPTION OF THE DRAWINGS

These and other features, aspects, and advantages of certain embodiments will become better understood when the following detailed description is read with reference to the accompanying drawings in which like characters represent like parts throughout the drawings.

FIGS. 18-20 show several possible arrangements of tanks, tank manifold skids, and a pump manifold skid in accordance with certain embodiments of the disclosure.

DETAILED DESCRIPTION

It is to be understood that the present disclosure provides many different embodiments, or examples, for implementing different features of various embodiments. Specific examples of components and arrangements are described below for purposes of explanation and to simplify the present disclosure. These are, of course, merely examples and are not intended to be limiting.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not mandate any particular orientation of the components.

Embodiments of the present disclosure generally relate to well testing operations at a wellsite. More particularly, at least some embodiments relate to a surface well testing apparatus that can be monitored and controlled remotely. For example, such a well testing apparatus can include a control and monitoring system that enables local control of the well testing apparatus. Additional embodiments include a well testing apparatus having a mobile monitoring system, in which operational information for the well test can be communicated to an operator via a mobile device.

Further, in some embodiments a well testing apparatus may be provided as a modular system to facilitate its transport to, and installation at, a wellsite. Such a modular well testing apparatus may include tank manifold skids and a pump manifold skid. The pump manifold skid can include manifolds for routing fluids received from a separator of the well testing apparatus and the tank manifold skids can be interconnected with each other to form manifolds for routing fluids between the pump manifold skid and fluid tanks connected to the manifolds of the interconnected tank manifold skids.

Figure 1:
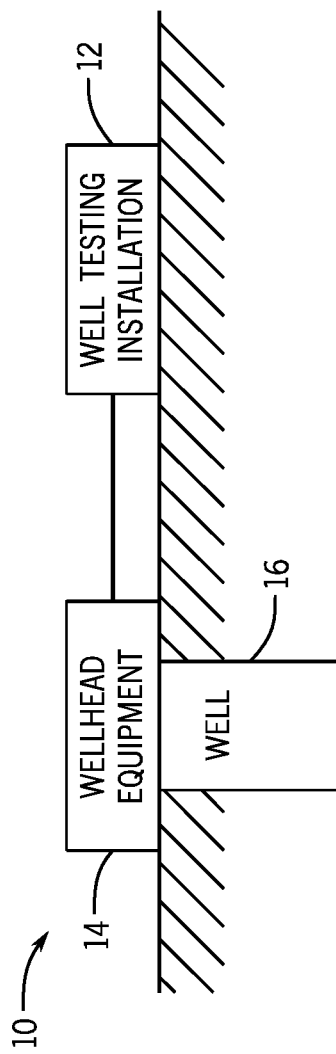
FIG. 1 generally depicts a well testing installation at a wellsite in accordance with an embodiment of the present disclosure.

Turning now to the drawings, a wellsite 10 is generally depicted in FIG. 1 in accordance with one embodiment. As presently shown, a well testing apparatus or installation 12 is deployed at the wellsite 10 and is coupled to wellhead equipment 14 installed at a well 16. The wellhead equipment 14 can include any suitable components, such as casing and tubing heads, a production tree, and a blowout preventer, to name but a few examples. Fluid produced from the well 16 can be routed through the wellhead equipment 14 and into the well testing apparatus 12. It will be appreciated that the wellsite 10 can be onshore or offshore. In offshore contexts, the well testing apparatus 12 can be installed on an offshore drilling rig at the wellsite 10.

In many cases, operation of a well testing apparatus can be split into four elementary functions: well control, separation, fluid management, and burning. In an example of a well testing apparatus 12 depicted in FIG. 2, these functions can be carried out by functional groups including a well control assembly 20, a separation portion 22, a fluid management assembly 24, and a burning operation portion 26. While certain elements of the well control apparatus 12 are shown in the present figure and discussed below, it is noted that the apparatus 12 may include other components in addition to, or in place of, those presently illustrated and discussed. For example, the well control apparatus 12 can include a gas specific gravity meter, a water-cut meter, a gas-to-oil ratio sensor, a carbon dioxide sensor, a hydrogen sulfide sensor, or a shrinkage measurement device. These and other components could be used at any suitable location within the well control apparatus 12, such as upstream or downstream of a separator (e.g., as part of the well control assembly 20 or the fluid management assembly 24).

Figure 2:
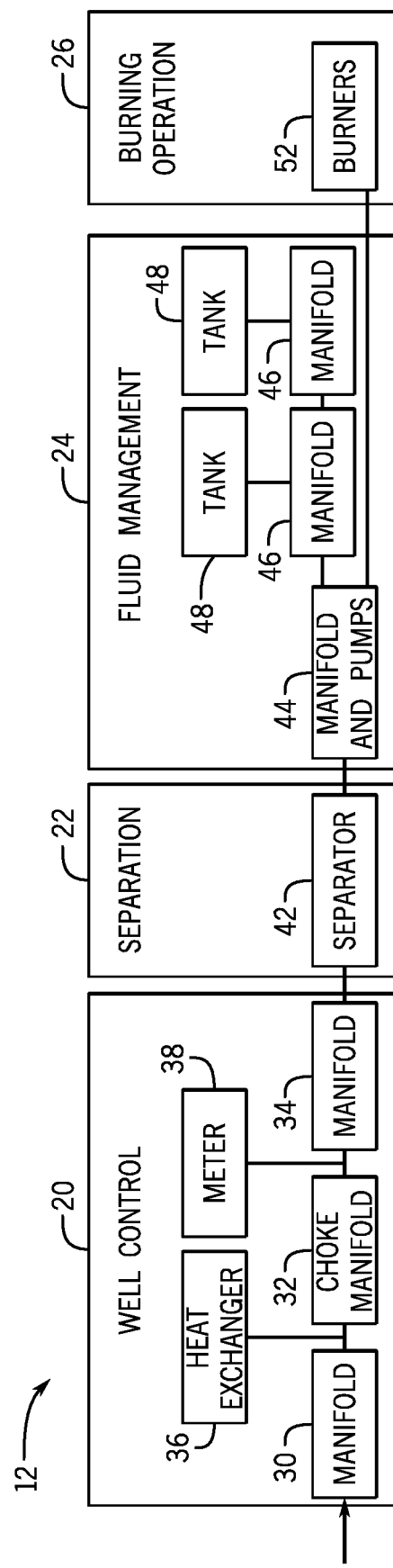
FIG. 2 is a block diagram representing functional groups of a well testing apparatus in accordance with an embodiment of the disclosure.

Effluents from the well 16 can be received in the well control assembly 20 and then routed to the separation portion 22 downstream of the assembly 20. The well control assembly 20 is shown in FIG. 2 as having flow control equipment in the form of various manifolds (i.e., an intake manifold 30, a choke manifold 32, and an additional manifold 34) for receiving and routing the well effluents. The depicted well control assembly 20 also includes a heat exchanger 36, which may be provided as a steam-heat exchanger, and a flow meter 38 for measuring flow of fluid through the well control assembly 20.

The well control assembly 20 conveys the effluents received from the well 16 to a separator 42. The features of the separator 42 can vary between embodiments. For example, the separator 42 can be a horizontal separator or a vertical separator, and can be a two-phase separator (e.g., for separating gas and liquids) or a three-phase separator (e.g., for separating gas, oil, and water) in different embodiments. Further, the separator 12 can include any of various mechanisms that facilitate separation of components of the incoming fluid, such as diffusers, mist extractors, vanes, baffles, and precipitators to name several examples.

In many instances, the well effluents are provided in the form of a multiphase fluid having a combination of oil, gas, and water. In at least some embodiments the separator 42 can be used to generally separate the multiphase fluid into its oil, gas, and water phases, and these separate fluids may be routed away from the separator 42 to the fluid management assembly 24. As will be appreciated by those skilled in the art, these separated fluids may not be entirely homogenous. That is, separated gas exiting the separator 42 can include some residual amount of water or oil and separated water exiting the separator 42 can include some amount of oil or entrained gas. Likewise, separated oil leaving the separator 42 can include some amount of water or entrained gas.

Referring again to FIG. 2, the separated fluids can be routed downstream from the separator 42 to the fluid management assembly 24. The fluid management assembly 24 includes flow control equipment, such as various manifolds and pumps (generally represented by block 44) for receiving fluids from the separator and conveying the fluids to other destinations, as well as additional manifolds 46 for routing fluid to and from fluid tanks 48. Although two manifolds 46 and two tanks 48 are depicted in FIG. 2, it is noted that the number of manifolds 46 and tanks 48 can be varied. For instance, in one embodiment the fluid management assembly 24 includes a single manifold 46 and a single tank 48, while in other embodiments the fluid management assembly 24 includes more than two manifolds 46 and more than two tanks 48.

The manifolds and pumps represented by block 44 can include a variety of manifolds and pumps, such as a gas manifold, an oil manifold, an oil transfer pump, a water manifold, and a water transfer pump. In at least some embodiments, the manifolds and pumps of block 44 can be used to route fluids received from the separator 42 to the fluid tanks 48 via the additional manifolds 46, and to route fluids between tanks 48. The manifolds and pumps of block 44 can also be used to route fluids received from the separator 42 directly to burners 52 for burning gas and oil (bypassing the tanks 48) or to route fluids from the tanks 48 to the burners 52.

As noted above, the components used in the apparatus 12 may vary between different applications. Still further, the equipment within each functional group of the well testing apparatus 12 may also vary. For example, the heat exchanger 36 could be provided as part of the separation portion 22, rather than of the well control assembly 20.

In certain embodiments, the well testing apparatus 12 is a surface well testing apparatus that can be monitored and controlled remotely. Remote monitoring of the well testing apparatus can be effectuated with sensors installed on various components of the functional groups of the apparatus, as discussed in greater detail below. In some instances, a monitoring system (e.g., sensors, communication systems, and human-machine interfaces) of the well testing apparatus 12 enables monitoring of each of its well control, separation, fluid management, and burning functions, though fewer functions could be monitored in other instances.

Figure 3:
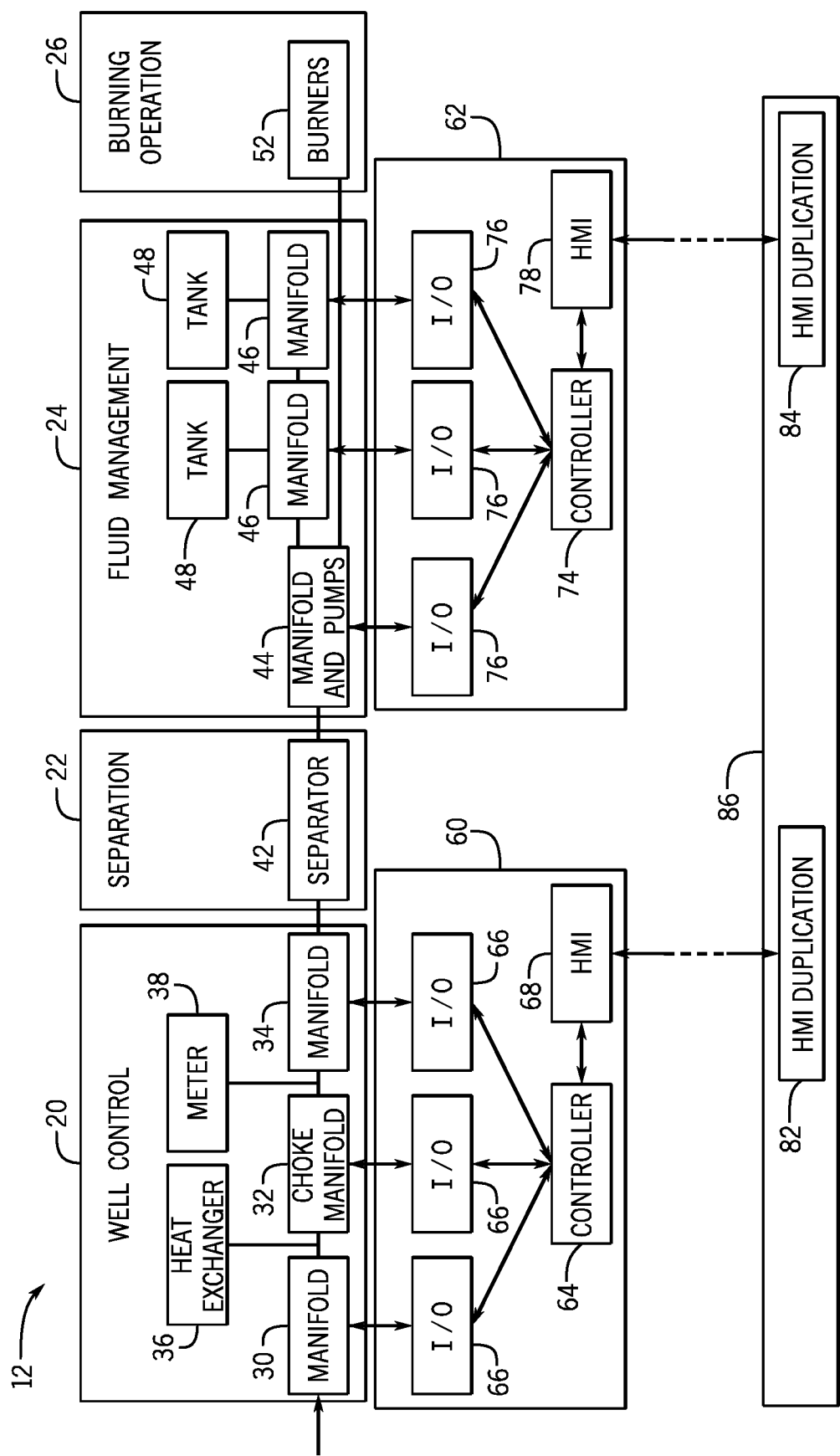
FIG. 3 depicts the functional groups of the well testing apparatus of FIG. 2 with control equipment for controlling certain well control and fluid management aspects of the well testing apparatus in accordance with an embodiment of the disclosure.

The well testing apparatus 12 may also include various control systems to enable remote control of components of the apparatus. For instance, the well testing apparatus 12 is shown in FIG. 3 as including control equipment 60 that enables remote control of components of the well control assembly 20, as well as control equipment 62 that enables remote control of components of the fluid management assembly 24. The control equipment 60 includes a controller 64 connected to various components of the well control assembly 20 via input/output modules 66. More specifically, the input/output modules 66 allow communication between the controller 64 and various sensors and actuators of the manifolds 30, 32, and 34. A human-machine interface (HMI) 68 allows communication between the controller 64 and an operator. Similarly, the control equipment 62 includes a controller 74 connected to various sensors and actuators of manifolds and pumps of the fluid management assembly 24 via input/output modules 76, as well as an HMI 78 that enables communication between the controller 74 and the same or a different operator.

The controllers 64 and 74 can be provided in any suitable form, such as programmable logic controllers. The HMIs 68 and 78 can also take any suitable forms, such as a device with display screens and physical keys or buttons, or devices with touchscreens that enable user input on the screens themselves. The HMIs 68 and 78 can display information to the operator, such as measurements or operational status of well control apparatus 12, while allowing the operator to provide commands (via user input) to the controllers 64 and 74.

In at least some embodiments, the well testing apparatus 12 enables local control of components of one or more of the functional groups of the apparatus 12. For example, the control equipment 60 can be provided locally as part of the well control assembly 20, and the control equipment 62 can be provided locally as part of the fluid management assembly 24, rather than providing the control equipment 60 and 62 at a location remote from the assemblies 20 and 24 (e.g., in a cabin at the wellsite). Indeed, as later discussed, the control equipment 60 and 62 can be mounted on skids shared with flow control equipment of the assemblies 20 and 24, respectively. The controllers 64 and 74 can operate as a local intelligence for controlling connected equipment of the assemblies 20 and 24. The local intelligence can be designed specifically for a given function of the well control apparatus (e.g., fluid management). With respect to the well control assembly 20, the local intelligence embodied in controller 64 can be used to actuate valves of the manifolds 30, 32, and 34, for instance. By way of further example, the local intelligence of controller 74 can be used to actuate pumps or valves of manifolds of the fluid management assembly 24.

In addition to the HMIs 68 and 78 that can be provided at or near equipment of the well testing apparatus 12, duplicate HMIs 82 and 84 can be provided away from the assemblies 20 and 24 at a control cabin 86 at the wellsite or some other location removed from the assemblies 20 and 24. The duplicate HMIs 82 and 84 provide redundancy, facilitating both local control at the equipment of the well testing apparatus 12 (via the HMIs 68 and 78) and global control from a location further away from the controlled equipment (via HMIs 82 and 84). This architecture allows the main control point for a given function (e.g., HMI 68 or 78) to be positioned next to the controlled equipment, while having a back-up control point in the control cabin or other location away from the controlled equipment. Further, controlling the flow control equipment or other equipment of the well testing apparatus 12 via HMI 68 or 78 positioned with the controlled equipment, rather than with HMI 82 or 84 removed from the controlled equipment, may allow an operator to directly sense certain contextual clues about operation of the well control assembly independent of the HMI 68 or 78 used by the operator. For example, while using the HMI 78, the operator may hear noises or feel vibrations from components of the well testing assembly 12. Such additional, sensory clues may provide insight into the operation of the well testing assembly 12 and inform decision-making by the operator regarding control of the assembly.

Although control equipment 60 and 62 enables local control of two functions of the well testing apparatus 12 (i.e., well control and fluid management), other embodiments may be configured to provide local control of a different number of functions. For instance, control equipment 60 or control equipment 62 could be omitted to provide local control of a single function of the apparatus 12, or additional control equipment could be provided for local control of other functions. Further, while the control equipment 60 and 62 may be used to control flow control equipment (e.g., manifolds and pumps) of the assemblies 20 and 24, the control equipment 60 and 62 could also or instead be used to control other components of the well testing apparatus 12.

In some embodiments the local intelligence is designed to control just a given elementary function, which offers flexibility to remotely control one or several elementary functions by varying the number of local intelligences coupled to components of the well testing apparatus 12. Furthermore, the equipment within a functional group may vary (e.g., the number of tanks for fluid management). To accommodate such variability, the hardware and software of the control system in at least some embodiments are modular. With respect to varying numbers of fluid tanks in the fluid management assembly 24, for instance, each fluid tank can be provided as part of an individual physical module (e.g., including a single manifold 46 and a single tank 48) and a corresponding software module can be implemented in configurable control software of the controller 74.

Figure 4:
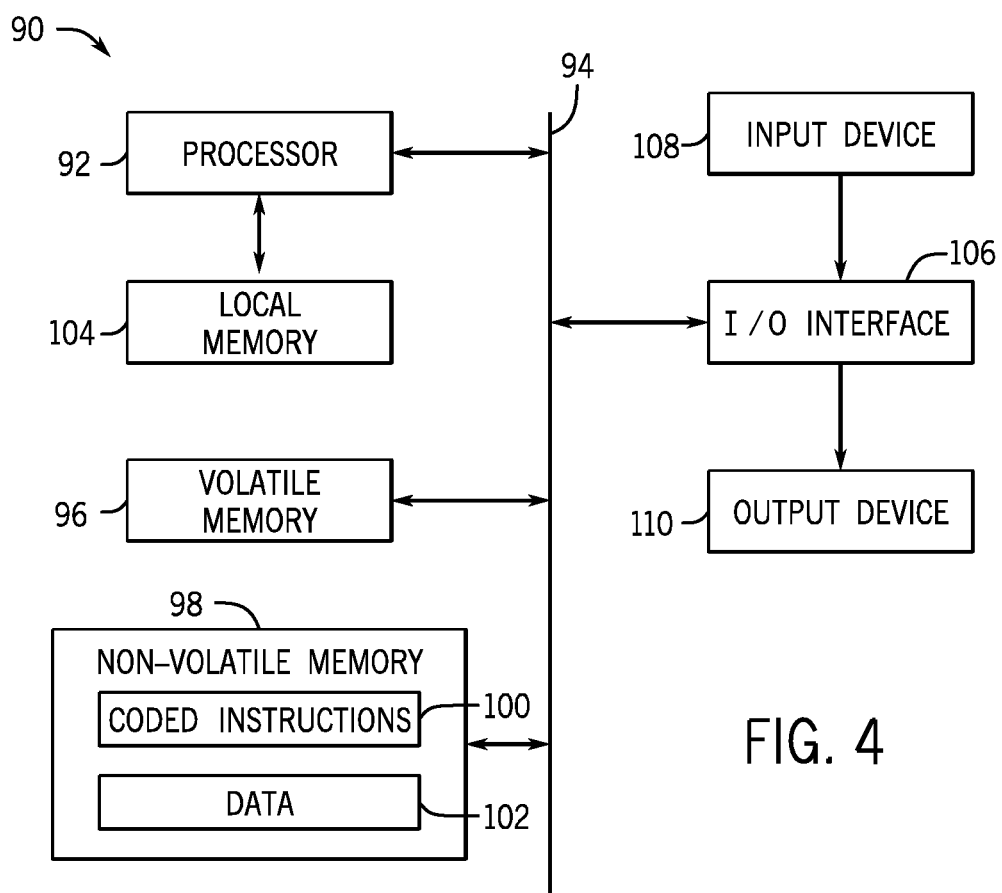
FIG. 4 is a block diagram of components of a processor-based system that can be used to perform certain monitoring or control operations in accordance with an embodiment of the disclosure.

The controllers 64 and 74, as well as various other data monitoring or control components discussed below, may be provided as processor-based systems. Such processor-based systems may include programmable logic controllers or programmed general-purpose computers, to name just two examples. An example of a processor-based system 90 is generally provided in FIG. 4. In this depicted embodiment, the system 90 includes at least one processor 92 connected by a bus 94 to volatile memory 96 (e.g., random-access memory) and non-volatile memory 98 (e.g., flash memory). Coded application instructions 100 (such as the programmed local intelligence of the controllers 64 and 74) and data 102 are stored in the non-volatile memory 98. The instructions 100 and the data 102 may also be loaded into the volatile memory 96 (or in a local memory 104 of the processor) as desired, such as to reduce latency and increase operating efficiency of the system 90. The coded application instructions 100 can be provided as software that may be executed by the processor 92 to enable various functionalities described herein. In at least some embodiments, the application instructions 100 are encoded in a non-transitory, computer-readable storage medium, such as the volatile memory 96, the non-volatile memory 98, the local memory 104, or a portable storage device (e.g., a flash drive or a compact disc).

An interface 106 of the system 90 enables communication between the processor 92 and various input devices 108 and output devices 110. The interface 106 can include any suitable device that enables such communication, such as a modem or a serial port. In some embodiments, the input and output devices 108 and 110 include controlled components of the well testing apparatus 12 and an HMI that enables communication between the system 90 and a user.

In various embodiments, controllers of the well testing apparatus 12, such as controllers 64 and 74, are configured (e.g., with programmed software) to control equipment of the apparatus 12 according to different modes. In one mode, which can be referred to as "manual remote control," an operator interacts with an HMI to control a given valve or other component of the well testing apparatus 12. For example, the operator may instruct a particular valve to open or close. In such an operating mode, the operator is fully responsible for the instructed action and there is no safety intelligence to support the decision or warn the operator of an improper command.

A different mode of operation, which can be referred to as "semi-automated remote control," is similar to the manual remote control mode noted above, but with local intelligence of a controller validating the operator's action against safety, quality, or other constraints. (These constraints can be stored as data in a memory of the controller.) For instance, one constraint may be that the operator may not open together a valve that would allow fluid to pass to a flare or other burner on a starboard side of a rig and a valve that would allow fluid to pass to a flare or other burner on the port side of the rig. That is, it can be undesirable to flare gas or burn oil on both the port and starboard sides of the rig simultaneously, and a constraint may be programmed into the control system so as to avoid such an occurrence.

Figure 5:
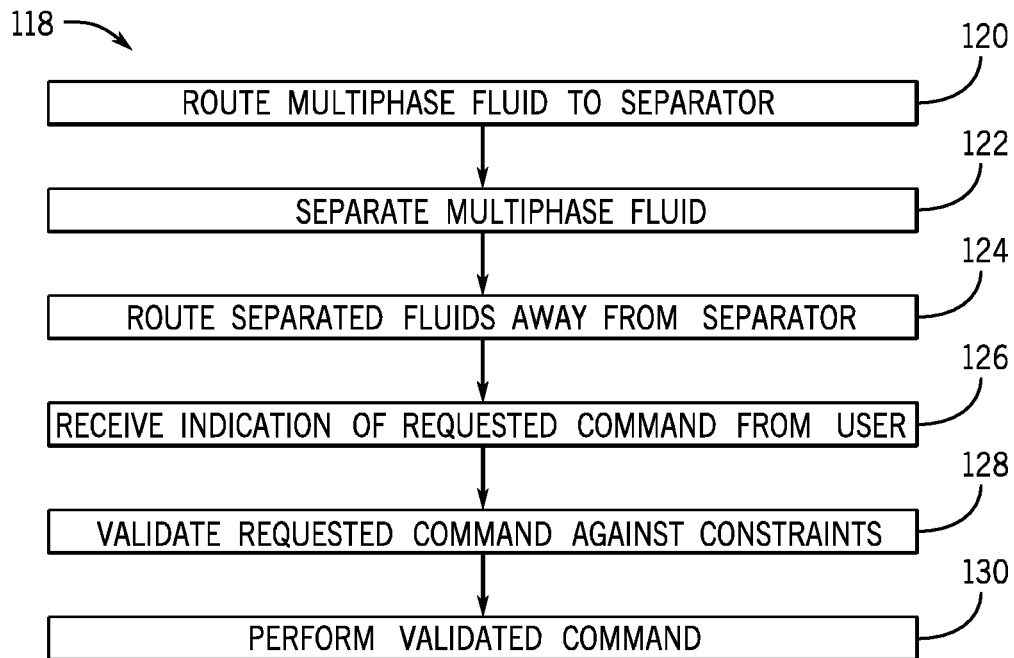
FIGS. 5 and 6 are flowcharts representing processes for controlling operation of a well testing apparatus in accordance with certain embodiments of the disclosure.

A further example of a semi-automated remote control process is generally represented by flowchart 118 in FIG. 5. In this embodiment, a multiphase fluid is routed to a separator (block 120), which separates the multiphase fluid (block 122) into separate fluids as described above. The separated fluids are routed away from the separator (block 124), such as to fluid tanks for storage or to burners or other destinations for disposal. The flow of the separated fluids downstream from the separator can be controlled by actuating pumps and valves of the fluid management assembly 24. Such flow can include routing of the separated fluids to a tank or to a disposal destination, routing separated fluids from a tank to a disposal destination, or routing separated fluids from one tank to another tank. The operator can indicate a requested command for controlling a valve or other component—such as opening or closing a valve or starting a pump—via an HMI in communication with the controller.

In a manual remote control mode, the controller may transmit an actuation signal to the controlled component in response to receipt of the user input of a requested command at the HMI. For example, a user can command a particular valve to open via the HMI, and the controller would then transmit an actuation signal to the valve actuator in response to the user input without considering the current operational status of other components of the well testing apparatus or the effect of actuating the valve as commanded. In contrast, in a semi-automated remote control mode, the received user indication of a requested command (block 126) is validated against constraints (block 128), such as with the local intelligence of the controller, so as to avoid undesired operation of the well testing apparatus. If the requested command would violate a given constraint—such as a safety constraint that one valve not be open at the same time as a particular different valve—the command would not be performed. In such a case, an error message could be provided to the operator via the HMI. The local intelligence in this example could assess the operating status of the two valves to determine whether a first of the two valves is closed before sending an actuation signal from the controller to the actuator of the second of the two valves to open the second valve. Once validated against the constraints, the requested command is performed (block 130) by sending the actuation signal to the controlled valve or other component.

Another mode of operation of the controller can be referred to as "automated remote control." In this control mode, the action of the operator from a remote control HMI launches a procedure resulting in multiple actions to be automatically performed by the controller. For example, an operator may select, via the HMI, an option to "transfer water from tank A to tank B" (e.g., the two fluid tanks 48 in FIG. 3). In response to this single selection, the controller may automatically send actuation signals to initiate a sequence of opening an inlet valve of tank B, opening an outlet valve of tank A, and starting a water pump, among other operations. Procedures can be programmed to line up a given flow path from a source (such as the separator 42 or a tank 48) to a destination (such as to another tank 48 or a burner 52) for a given fluid (such as oil).

Figure 6:
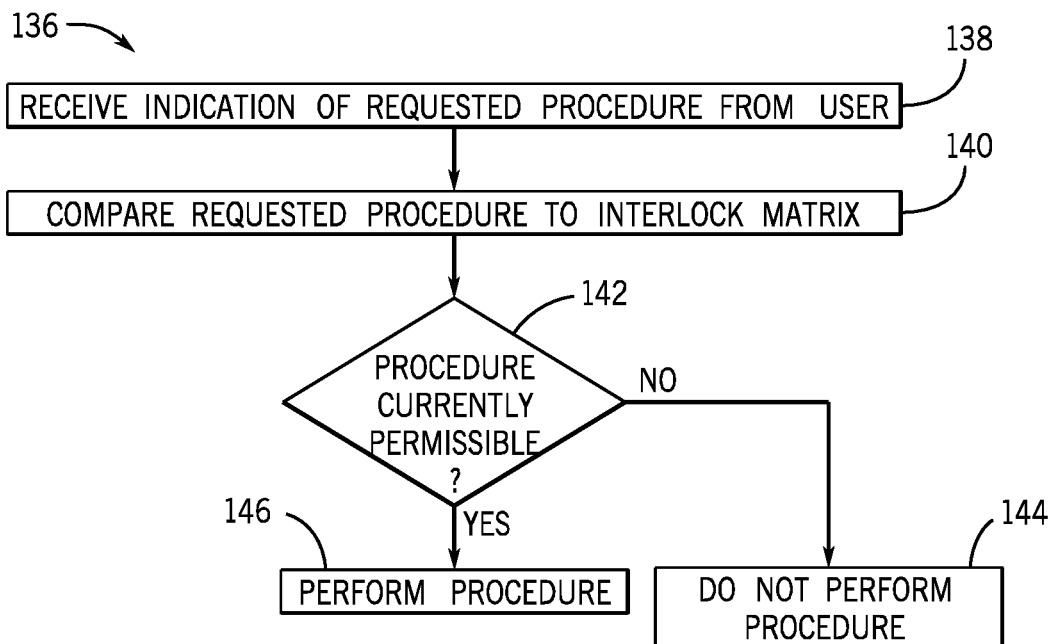

An example of an automated remote control process is generally represented by flowchart 136 in FIG. 6. In this embodiment, an indication of a user-requested operational procedure is received (block 138), such as through user input at a remote control HMI. In the automated remote control mode, the requested procedure can be automatically compared to an interlock matrix (block 140) to prevent the launch of incompatible sequences together (such as "flow oil to burner port side" and "flow gas to flare starboard side"). This is generally represented by decision block 142, in which local intelligence can determine whether the requested operational procedure is permissible (e.g., whether it is compatible or incompatible with another procedure being performed or with the current operational state of the well testing apparatus). If the requested procedure is not permissible, the controller does not perform the procedure (block 144) and an error message can be given to the operator. If the requested procedure is determined to be permissible, it is then automatically performed (block 146), such as by sending actuation signals to the components to be controlled. It is further noted that the controller can include an event logger that records events, operator actions, error messages, and alarms for the control system.

Surface well testing installations may use a large deck space to spot and fix equipment and interconnect them with piping. As discussed above, the well testing apparatus 12 may take many forms. As one example, the well testing apparatus 12 may be provided in the form of a surface well testing system or apparatus 150 generally illustrated in FIG. 7. In this depicted embodiment, a multiphase fluid (represented here by arrow 152) enters a flowhead 154 and is routed to a separator 170 through a surface safety valve 156, a steam-heat exchanger 160, a choke manifold 162, a flow meter 164, and an additional manifold 166. The apparatus 150 in FIG. 7 also includes a chemical injection pump 158 for injecting chemicals into the multiphase fluid flowing toward the separator 170.

In the presently depicted embodiment, the separator 170 is a three-phase separator that generally separates the multiphase fluid into gas, oil, and water components. The separated gas is routed downstream from the separator 170 through a gas manifold 174 to either of the burners 176 for flaring gas and burning oil. The gas manifold 174 includes valves that can be actuated to control flow of gas from the gas manifold 174 to one or the other of the burners 176. Although shown next to one another in FIG. 7 for clarity, the burners 176 may be positioned apart from one another, such as on opposite sides of a rig.

Figure 7:
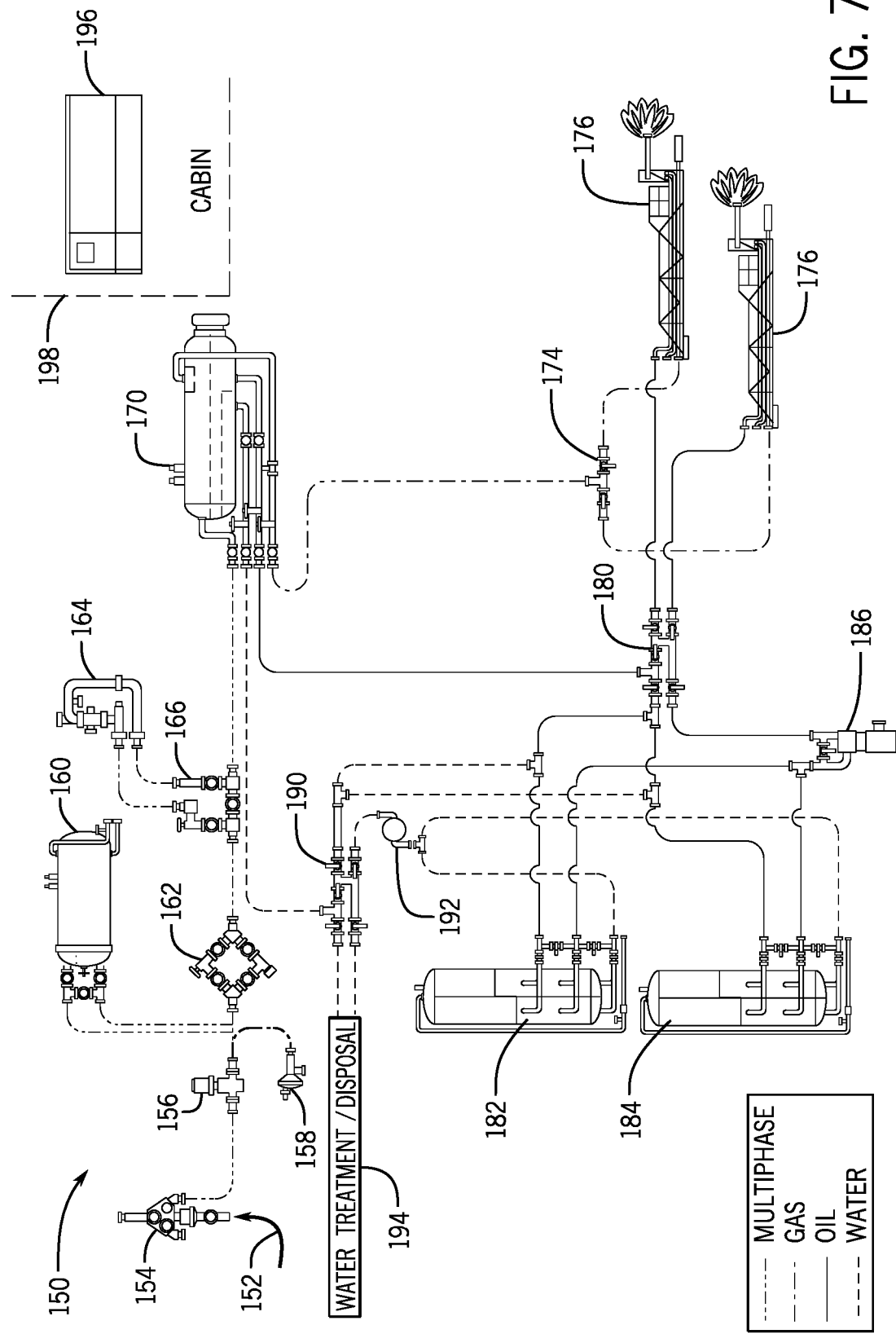
FIG. 7 depicts various equipment of a well testing apparatus in accordance with an embodiment of the disclosure.

The separated oil from the separator 170 is routed downstream to an oil manifold 180. Valves of the oil manifold 180 can be operated to permit flow of the oil to either of the burners 176 or either of the tanks 182 and 184. The tanks 182 and 184 can take any suitable form, but are depicted in FIG. 7 as vertical surge tanks each having two fluid compartments. This allows each tank to simultaneously hold different fluids, such as water in one compartment and oil in the other compartment. An oil transfer pump 186 may be operated to pump oil through the well testing apparatus 150 downstream of the separator 170. The separated water from the separator 170 is similarly routed to a water manifold 190. Like the oil manifold 180, the water manifold 190 includes valves that can be opened or closed to permit water to flow to either of the tanks 182 and 184 or to a water treatment and disposal apparatus 194. A water transfer pump 192 is used to pump the water through the system.

As will be appreciated, the well test area in which the well testing apparatus 150 (or other embodiments of a well testing apparatus) is installed may be classified as a hazardous area. In some embodiments, the well test area is classified as a Zone 1 hazardous area according to International Electrotechnical Commission (IEC) standard 60079-10-1: 2015. The various equipment of the well testing apparatuses described herein, including flow control equipment and controllers, may be positioned within such a Zone 1 hazardous area.

Referring again to FIG. 7, a cabin 196 at the wellsite may acquire data from the well testing apparatus 150. This acquired data can be used to monitor and control the well testing apparatus 150. In at least some instances, the cabin 196 is set apart from the well test area having the well testing apparatus 150 in a non-hazardous area. This is represented by the dashed line 198 in FIG. 7, which generally serves as a demarcation between the hazardous area having the well testing apparatus 150 and the non-hazardous area of the cabin 196.

The equipment of a well testing apparatus is monitored during a well testing process to verify proper operation and facilitate control of the process. Such monitoring can include taking numerous measurements during the well test, examples of which include choke manifold temperature and pressures (upstream and downstream), heat exchanger temperature and pressure, separator temperature and pressures (static and differential), oil flow rate and volume from the separator, water flow rate and volume from the separator, and fluid levels in tanks of the apparatus. In some instances, these data are recorded manually by an operator who walks around the well test area and records the measurements and other process information on a sheet of paper (e.g., a reading sheet) to inform future decision-making regarding control of the well test. With the various equipment of the well testing apparatus spread about the well test area, such manual measurement collection can be time-consuming. Taking care to avoid tripping hazards in the well test area and climbing up vertical tanks to read fluid levels in the tanks further increase the time spent manually collecting the process information.

In accordance with at least some embodiments of the present technique, however, a mobile monitoring system is provided with a surface well testing installation. This enables monitoring of the well test process on a mobile device (e.g., a mobile device suitable for use in Zone 1 hazardous area, like the well test area). Various information can be automatically acquired by sensors and then presented to an operator via the mobile device. The mobile monitoring system may provide various functions, such as a sensor data display, video display, sensor or video information interpretation for quality-assurance and quality-control purposes, and a manual entry screen (e.g., for a digital tally book for recording measurements taken by the operator). Further, the monitoring system can be modular and configurable so it may be implemented on any well testing installation that is equipped according to the present techniques.

Figure 8:
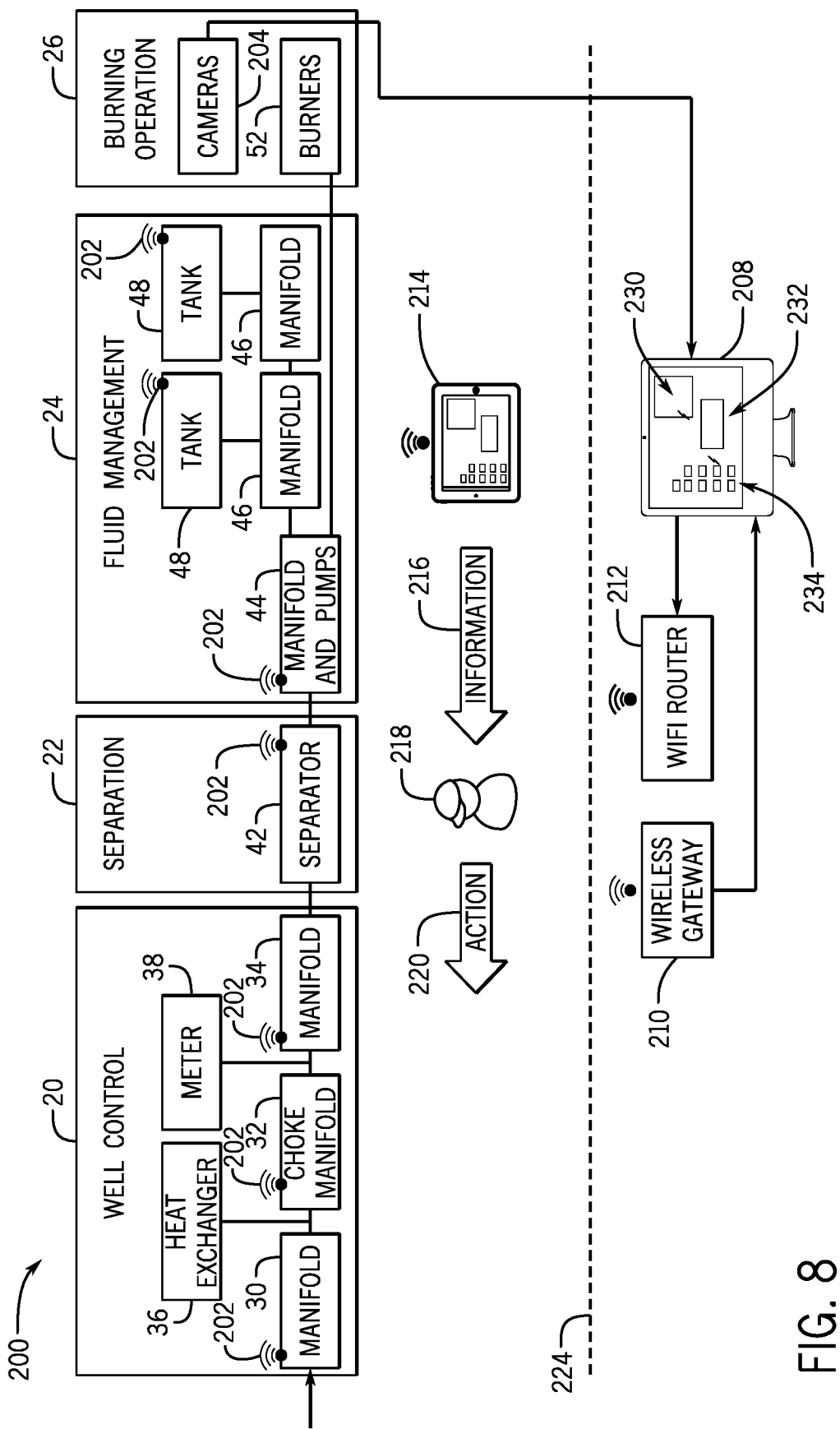
FIG. 8 is a diagram illustrating a mobile monitoring system with a well testing apparatus in accordance with an embodiment of the disclosure.

An example of a mobile monitoring system 200 is generally depicted with a well testing apparatus in FIG. 8. As noted above, a well testing apparatus 12 may be split into four elementary functions (well control, separation, fluid management, and burning operation), and the equipment used in the apparatus 12 for each function can vary between embodiments. The well testing apparatus depicted in FIG. 8 includes the same functional groups and equipment described above with respect to FIG. 2, but is equipped with data acquisition devices in the form of sensors 202 and cameras 204 for monitoring the well testing functions. In the presently depicted embodiment, the sensors 202 and cameras 204 are deployed to enable monitoring of each of the well testing functions presented above. More specifically, the sensors 202 are installed on various components of the well testing equipment and the cameras 204 may be positioned next to booms of the burners 52 to capture image data (e.g., video) of burner operation. In other embodiments, however, a mobile monitoring system could be used to monitor fewer well testing functions. And while the system depicted in FIG. 8 includes cameras 204 for monitoring the burning operation function and sensors 202 for monitoring components of the well control, separation, and fluid management functions, it will be appreciated that sensors 202 can be used to monitor the burning operation function and that cameras 204 can be used to monitoring the well control, separation, and fluid management functions. Various data may be acquired with the sensors 202 and cameras 204, non-limiting examples of which include pressure measurements, temperature measurements, flow rates, top and interface fluid levels in tanks, and image data (static or video).

The data acquired by the sensors 202 and cameras 204 is communicated to a computer system 208, which may process and store the received data. In the presently depicted embodiment, the sensors 202 are wireless sensors that wirelessly transmit data to the computer system 208 via a wireless gateway 210. Any suitable wireless communication standard may be used; in at least one instance, the sensors 202 are HART® wireless sensors and the wireless gateway is a HART® wireless gateway. Although the sensors 202 are shown as wireless sensors in FIG. 8, it is noted any of these sensors 202 could instead be provided as a wired sensor in communication with the computer system 208. Further, the cameras 204 can transmit data in any suitable manner. Although data from the cameras 204 could be transmitted wirelessly, in at least some embodiments the cameras 204 send video or other data to the computer system 208 over a wired connection.

The computer system 208 communicates information based on the data acquired with the sensors 202 or cameras 204 to a mobile device 214 over a wireless network via a wireless access point, such as a WI-FI® router 212. In some instances, the wireless network can include wireless repeaters to improve communication signal range and strength within the well test area. In one embodiment, the mobile device 214 may receive wirelessly transmitted data directly from one or more sensors 202 or cameras 204.

The mobile device 214 can be carried by an operator 218 within a well test area. The mobile device 214 is a human-machine interface that includes a screen for showing information about a well testing process. More specifically, the mobile device 214 is configured to display information (generally represented by arrow 216) on the screen to the operator 218 about the operation of the well testing apparatus based on the data acquired with the sensors 202 or cameras 204. This enables mobile monitoring of the operation of the well testing apparatus by the operator as the operator moves about the well test area. In at least some embodiments, the mobile device displays such information in real time, thus enabling real-time mobile monitoring of the well testing process by an operator in the well test area. Any type of information may be displayed, such as sensor data from sensors 202, video captured by the cameras 204, processed data, or interpreted data. Examples of such interpreted data include information regarding choke plugging, choke erosion, carry-over, carry-under, and emulsion detection and characterization in tanks. Additionally, by displaying such process information on the mobile device 214, the operator 218 can assess the urgency of the process status, prioritize tasks, and take appropriate action (generally represented by arrow 220), such as opening or closing valves, in a timely manner. Alarms may also be displayed, and alarms and alarm management actions (such as acknowledgement or reset) can be recorded in an event logger.

In at least some embodiments, the mobile device 214 is certified for usage in Zone 1 hazardous areas and is carried by an operator 218 within a Zone 1 hazardous area (e.g., the well test area), while the computer system 208 is located in a non-hazardous area (e.g., a lab cabin). Dashed line 224 in FIG. 8 generally represents a boundary between these hazardous and non-hazardous areas. Although a single mobile device 214 is shown in FIG. 8 for simplicity, it will be appreciated that the mobile monitoring system could include multiple mobile devices 214 (which could be carried by different operators) that receive well test process information from the computer system 208. Mobile devices 214 could take any suitable form, such as tablet computers or smartphones. Further, the computer system 208 and mobile devices 214 are processor-based systems that include various processing and memory components, such as those described above with respect to system 90 of FIG. 4. Software or other coded instructions resident in the computer system 208 or mobile devices 214 can be used to facilitate the mobile monitoring and control functionalities described herein. Information can be displayed to a user on a screen of the computer system 208 or of a mobile device 214 in any suitable manner, such as via a webpage or a mobile device application.

As discussed above, information based on data acquired with the sensors 202 and the cameras 204 can be displayed to users of the computer system 208 or mobile devices 214. In some embodiments, including that illustrated in FIG. 8, the computer system 208 and the one or more mobile devices 214 are configured to display video 230 in a window on their respective screens, while also displaying additional information (e.g., information 232 and 234) on their screens based on data acquired from one or more sensors 202. In other instances, the video 230 and the additional information 232 and 234 could be displayed at different times, such as consecutively rather than concurrently. While the computer system 208 and the mobile device 214 are depicted in FIG. 8 as displaying identical graphical information on their screens (i.e., video 230 and information 232 and 234), the content of the information displayed on their screens may differ in other instances. For example, less information may be displayed on the screen of the mobile device in some cases due to screen size constraints.

In order to constantly monitor burning operations, the monitoring system 200 can include at least one camera 204 pointed to each burner. In one embodiment, two cameras 204 are pointed to a first burner 52 and two other cameras 204 are pointed to a second burner 52. The cameras 204 (which can detect visible or infrared light) are positioned to acquire image data (video or static) about operation of the burners 52 during burning of oil or gas. The acquired image data can be displayed on a screen of the computer system 208 (such as in a lab cabin) or on a mobile device 214 in the well testing area. The cameras 204 can be individually controlled from the computer system 208 (or from a mobile device 214) to pan, tilt, or zoom the cameras. In at least some embodiments, the video data acquired with the cameras 204 has high-definition resolution (e.g., 720$p$) and a frame rate of at least 25 frames per second. The cameras 204 can also include microphones, and sound captured by these microphones can be transmitted to the computer system 208 and made available to users (e.g., in the lab cabin). The video and sound captured with the cameras 204 and transmitted to the computer system 208 may be recorded for future use, such as for replay, traceability, contractual engagement, and post-job troubleshooting.

Figure 9:
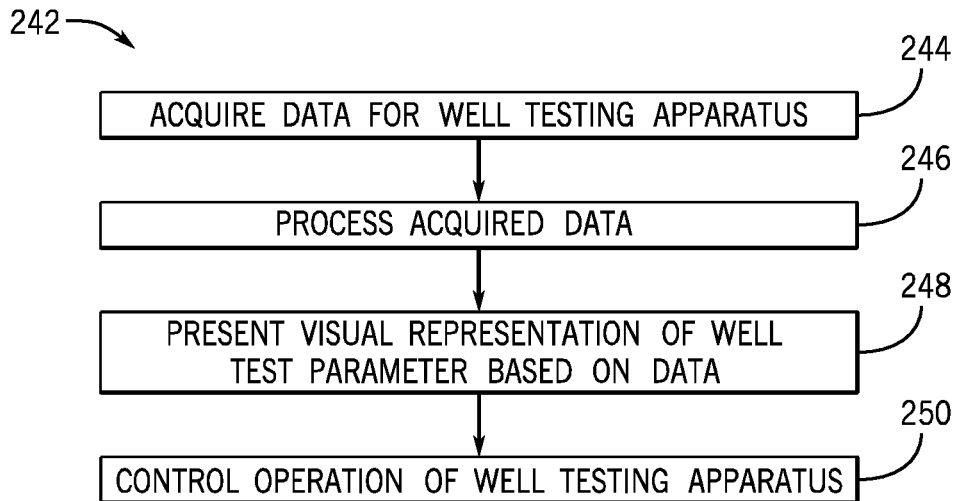
FIG. 9 is a flowchart representing a process for conveying well test information to an operator via a mobile device and controlling a well test apparatus in accordance with an embodiment of the disclosure.

By way of further example, a process for conveying well test information via a mobile device is generally represented by flowchart 242 in FIG. 9. This embodiment includes acquiring data (block 244) for a well testing apparatus during a well test, such as with a sensor 202. The acquired data is transmitted to a data acquisition system, such as the computer system 208 or the mobile device 214, which processes the acquired data (block 246). Such processing can include any of a variety of actions, such as storing the data, analyzing the data, interpreting the data, or forwarding the data to another device or location. The process represented in FIG. 9 also includes presenting a visual representation (block 248) of a well test parameter on a display of a mobile device (e.g., mobile device 214) present at the wellsite based on the processed data. This can include, for example, displaying real-time values of well test measurements directly acquired by sensors 202 or interpreted from measurements taken by the sensors 202. In some instances, processing the data in block 246 includes identifying trends in the data, and a visual representation of this identified trend may then be presented on a screen of the mobile device 214 or of the computer system 208.

The process represented in FIG. 9 also includes controlling operation of the well testing apparatus (block 250), such as in response to information provided to an operator via the computer system 208 or mobile device 214. In some instances, an operator may manually control operation, such as by walking to a particular valve of the well testing apparatus and then opening or closing the valve. In other instances, however, the well testing apparatus may include remote control functionality, such as that described above, and an operator may initiate control via a human-machine interface. In one such embodiment, the control can be effected by an operator through user input to a mobile device 214 carried by the operator. That is, the mobile device 214 may communicate a command to a controller (e.g., controller 74) to actuate a component or begin an actuation sequence for multiple components.

Additionally, in some embodiments the mobile device 214 can be used as a digital tally book for manual data recording by an operator. For example, the operator can collect well test measurements (such as measurements of fluid properties) independent of the mobile device 214, and then enter those measurements in the mobile device 214. The data entered into the mobile device 214 can be transmitted to another system (e.g., computer system 208) in a real-time or delayed manner.

Figure 10:
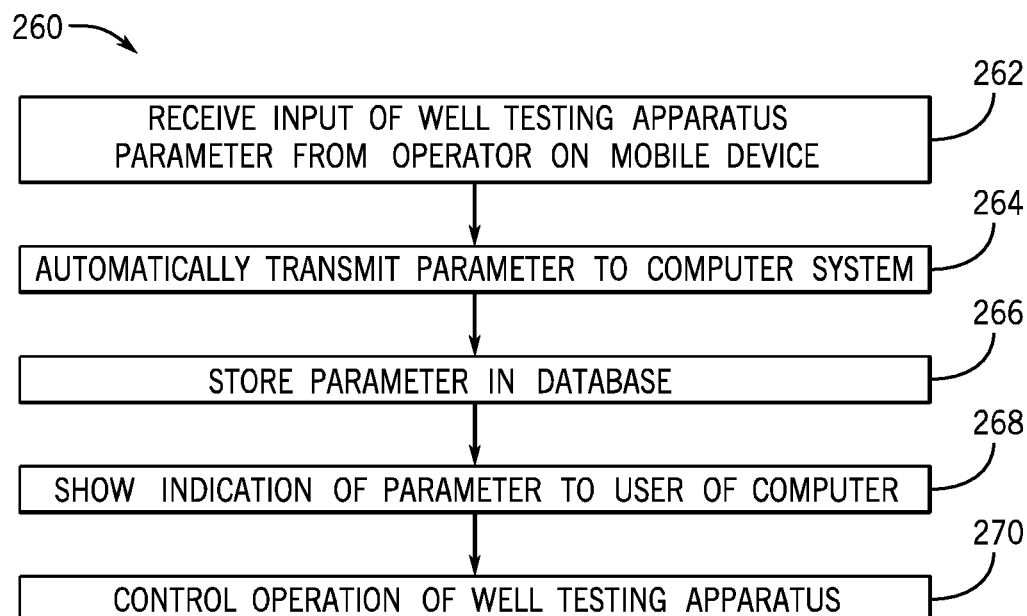
FIG. 10 is a flowchart representing a process for recording and transmitting well test operational data via a mobile device in accordance with an embodiment of the disclosure.

An example of a process for recording and transmitting well test operational data via a mobile device is generally represented by flowchart 260 in FIG. 10. This embodiment includes receiving from an operator, on a mobile device (such as mobile device 214), input of an operational parameter measured by the operator during a well test (block 262). The process also includes automatically transmitting the measured parameter to a computer system (e.g., computer system 208) during the well test (block 264). In at least one embodiment, the measured parameter is transmitted from the mobile device to the computer system over a wireless network. The measured parameter can be stored (block 266) in a database of well test operational data. The measured parameter can also be processed by the computer system and an indication of the measured parameter can be shown (block 268) to a user of the computer system. The process represented in FIG. 10 also includes controlling operation of the well testing apparatus (block 270). For example, a user of the computer system can input a command to remotely control the well testing apparatus based on the indication of the measured parameter, and a controller of the well testing apparatus can send an actuation signal to one or more components in response to the command.

The mobile monitoring embodiments discussed above enable information about a well testing apparatus to be conveyed to an operator within a well test area in charge of control of a well test operation. Among other things, this may facilitate increased understanding and awareness among operators of the current status of the operation to aid in making control decisions. Certain embodiments of the mobile monitoring systems may also improve operational quality and safety, such as by reducing tripping hazards in the well test area (as the operator does not have to go read each sensor), reducing working at height hazards (the operator does not have to climb up vertical tanks to read fluid levels), reducing pollution risk (early detection of non-efficient burning conditions), and improving data-based decision-making processes (process overview and interpreted diagnostic information may enable decisions to be made in a more timely manner).

As noted above, the well testing apparatus 12 of some embodiments can be provided as a modular system in which modules for performing various functions of the well testing apparatus 12 are assembled together and then used for well testing operations at a wellsite. For example, a well testing apparatus 12 can include a pump manifold skid and a tank manifold skid, as described in greater detail below. In at least some embodiments, these skids gather the piping-related equipment (valves, fixed piping lines) and the pumps (water and oil transfer pumps) that enable the management of single phase fluids downstream of a separator. The pump manifold skid can include automated manifolds and pumps to route fluids between separators, tanks, and disposal equipment (e.g., flares and other burners). The tank manifold skid connects to a fluid tank, such as a two-compartment tank, and includes actuated valves that enable opening and closing the inlet, outlet, and drain for each compartment. A control system can be integrated on these skids, and in at least one embodiment includes a local intelligence installed on the pump manifold skid. In some instances, a single pump manifold skid is used in a well testing apparatus 12, while the number of tank manifold skids is equal to the number of fluid tanks deployed in the apparatus to receive fluid from the pump manifold skid. Each tank manifold skid may be self-contained and may include the associated control system accessories used to operate and control the valves.

Equipment footprint optimization may be desirable, particularly in locations where space is limited, such as on offshore rigs. Reduction in rig up/rig down time and minimal manual intervention may also be desirable, since they can be directly correlated to cost savings. In at least some embodiments, these skids are designed to reduce the surface well testing installation footprint, to reduce the rig up/rig down time and effort, and to be modular in terms of layout, and are also automated to reduce manual intervention during operations. The modularity of these skids allows them to be assembled in different configurations to accommodate the varied spatial constraints for different rigs and to accommodate the varied processes for different well tests.

These skids can also be designed for use in offshore conditions (roll, pitch, heave, etc.). For such offshore uses, the skids can be secured to a rig platform with clamps. Bumper protection may be provided on the skids and accessories such as guides may be provided for ease of installation with a crane in sea conditions (roll, pitch, etc.). In some embodiments, the tank manifold skids are connected to the tanks and to each other with rigid bolted connections to distribute the deck load. The skids may be designed to withstand the transit, environmental, and fatigue loads, such as stipulated in DNVGL-OS-E101 (promulgated in July 2015 by DNV GL Group) for temporary offshore well test installations.

Further, in some embodiments the skids can be pre-assembled with piping and a pneumatic and electrical control system; in such cases, installation may be limited to interconnecting piping, pneumatic hoses, and electrical cables with connectors. Any desired walkways for facilitating access by operators can be installed in a fixed manner without bolting. In further embodiments, the tank manifold skids and the pump manifold skid have automated equipment and a control system to enable remote control, such as described above.

Figure 11:
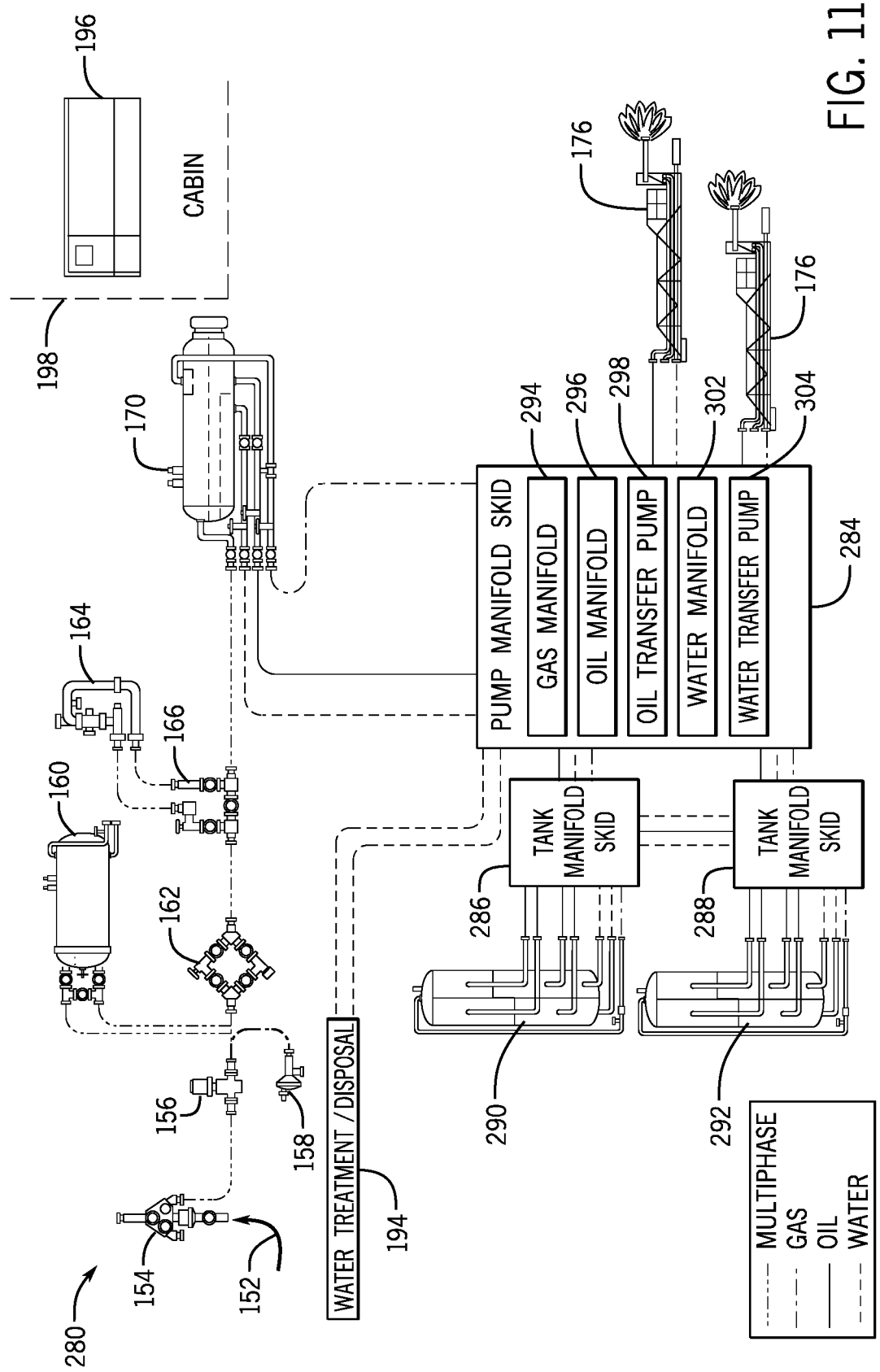
FIG. 11 depicts various equipment of a well testing apparatus, including a pump manifold skid and tank manifold skids, in accordance with an embodiment of the disclosure.

By way of example, the well testing apparatus 12 may be provided in the form of a surface well testing apparatus 280, as generally depicted in FIG. 11. The well testing apparatus 280 is generally similar to the well testing apparatus 150 described above and includes many of the same components. But rather than having gas manifold 174, oil manifold 180, oil transfer pump 186, water manifold 190, and water transfer pump 192 separately positioned about the well test area, the well testing apparatus 280 includes a pump manifold skid 284 on which various manifolds and pumps are mounted. More specifically, the flow control components mounted on the pump manifold skid include a gas manifold 294, an oil manifold 296, an oil transfer pump 298, a water manifold 302, and a water transfer pump 304 for routing gas, oil, and water between the separator 170, tanks 290 and 292, the burners 176, and water disposal equipment 194.

The depicted well testing apparatus 280 also includes tank manifold skids 286 and 288 that route fluid between the pump manifold skid 284 and connected tanks 290 and 292. The tanks 290 and 292 are generally depicted in FIG. 11 as two-compartment, vertical surge tanks, though they could take different forms in other embodiments. Further, the number of tanks 290 and 292 and the number of associated tank manifold skids 286 and 288 may also vary between embodiments. In at least some instances, the number of such fluid tanks is equal to the number of the tank manifold skids and each fluid tank has its own tank manifold skid. That is, the tank manifold skids are connected to associated tanks in a one-to-one ratio. Other embodiments may include a different ratio of tank manifold skids and associated tanks, such as one-to-two, one-to-three, or one-to-four.

Figure 12:
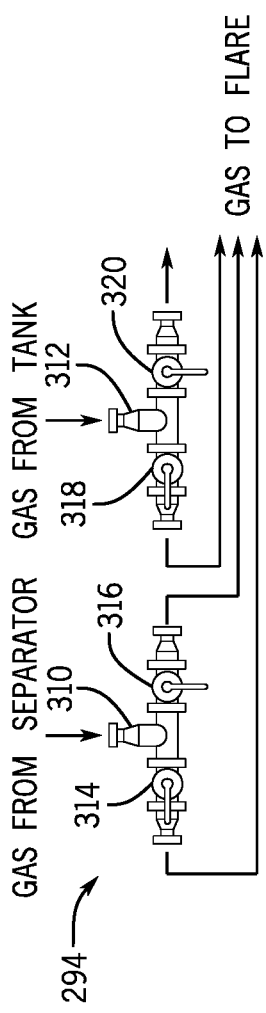
FIGS. 12-14 depict various manifolds that can be mounted on the pump manifold skid of FIG. 11 in accordance with certain embodiments of the disclosure.
Figure 14:
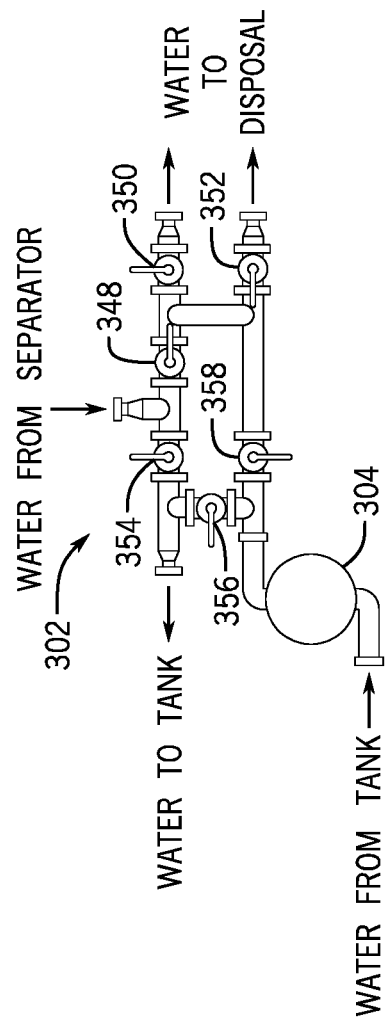
Figure 13:
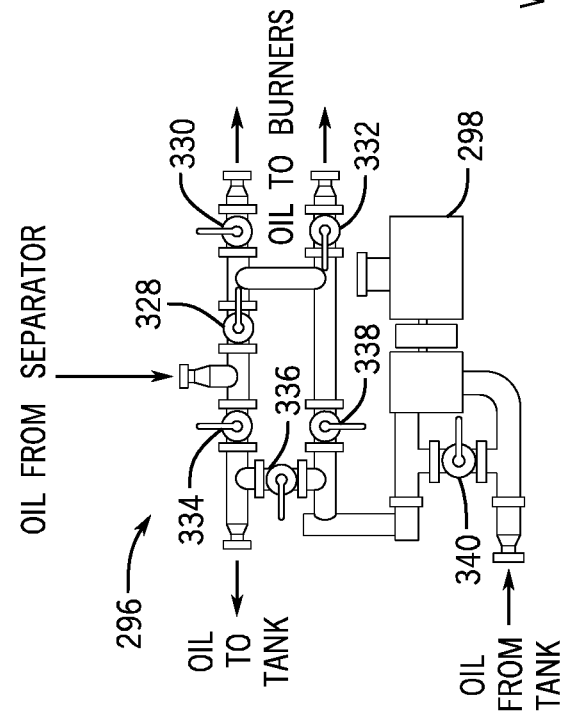

Examples of manifolds and pumps mounted on the pump manifold skid 284 are depicted in FIGS. 12-14 in accordance with certain embodiments. The gas manifold 294 is depicted in FIG. 12 as having a first manifold portion 310 that receives generally higher pressure gas from the separator 170 and a second manifold portion 312 that receives generally lower pressure gas from the tanks (e.g., tanks 290 and 292). Valves 314, 316, 318, and 320 can be operated (manually or via remote control) to selectively route gas to a desired burner 176 (e.g., port or starboard) for flaring. The oil manifold 296 is depicted in FIG. 13 as having pipework and valves 328, 330, 332, 334, 336, and 338. These valves can be operated (manually or via remote control) to route oil between various locations, such as from the separator to the tanks, from the tanks to a desired burner 176, or between two tanks. The oil transfer pump 298 can pump oil through the system and is shown in FIG. 13 as including a bypass valve 340. The water manifold 302 is depicted in FIG. 14 as having pipework and valves 348, 350, 352, 354, 356, and 358. These valves can be operated similarly to those of the oil manifold to route water between various locations (e.g., from the separator to the tanks, from the tanks to disposal, and between two tanks). The water transfer pump 304 can be used to pump water through the system. In at least some embodiments, the valves of the manifolds 294, 296, and 302 are pneumatically actuated and are operated and controlled using a control system, such as that described above.

Figure 15:
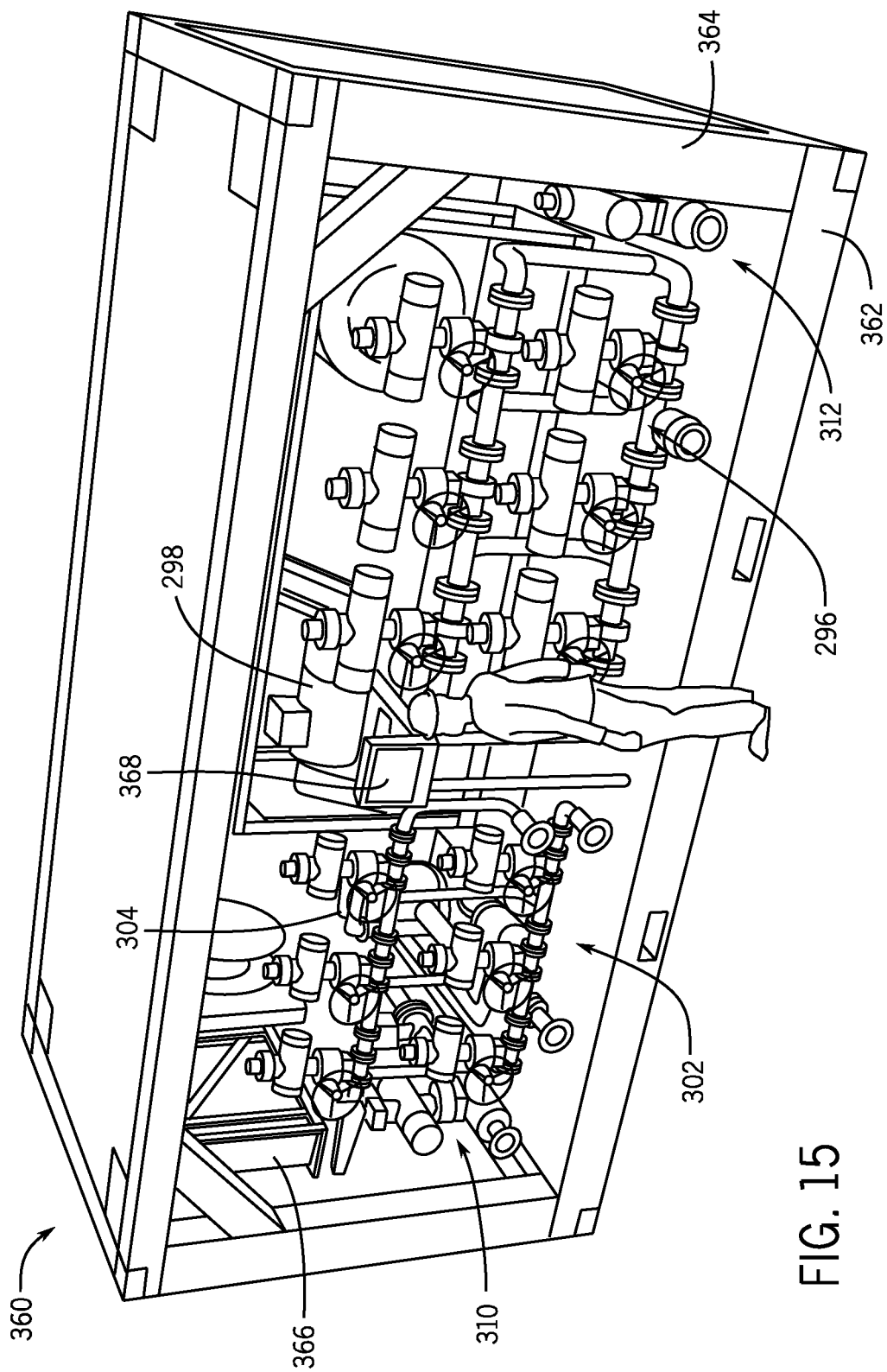
FIG. 15 depicts a pump manifold skid in accordance with an embodiment of the disclosure.

In FIG. 15, an implementation 360 of the pump manifold skid 284 is depicted as having a platform 362 and a frame 364. This implementation of the pump manifold skid 284 is designed for use on offshore rigs and can accommodate roll, pitch, and heave conditions on such rigs (e.g., in accordance with offshore standard DNVGL-OS-E101). The platform 362 is depicted as having slots to facilitate transport and handling of the skid 284. The gas manifold 294 (with its portions 310 and 312), the oil manifold 296, the oil transfer pump 298, the water manifold 302, and the water transfer pump 304 are shown mounted on the platform 362. The pump manifold skid 284 includes the power system (electrical, pneumatic), the communication system, and the control system, and various components of these systems may be installed in enclosures mounted on the skid 284. For example, a control unit (e.g., controller 74) and communication devices may be mounted in a control box 366.

The implementation of the pump manifold skid depicted in FIG. 15 also includes an HMI in the form of a control panel 368. As presently shown, the control panel 368 includes a screen for displaying information to an operator. The control panel is mounted on the skid such that it is easily accessible. In at least some embodiments, the pumps and valves of the pump manifold skid and the tank manifold skids (as described below) can be actuated from the control panel 368 or from a lab cabin (e.g., via computer system 208). In another embodiment, these pumps and valves can be actuated from a mobile device 214 carried by an operator, as discussed above. It is also possible to connect external back-up pumps for oil or water transfer. Cables and other accessories used for the control system can be included in the pump manifold skid 284. For example, the skid 284 may include cables to be connected to tank manifold skids so as to enable communication of control signals from the control unit mounted on the pump manifold skid 284 to actuators of valves mounted on the tank manifold skids so as to selectively control flow of fluids between components (e.g., between the separator 170 and tanks 290 and 292) of the well testing apparatus.

Figure 16:
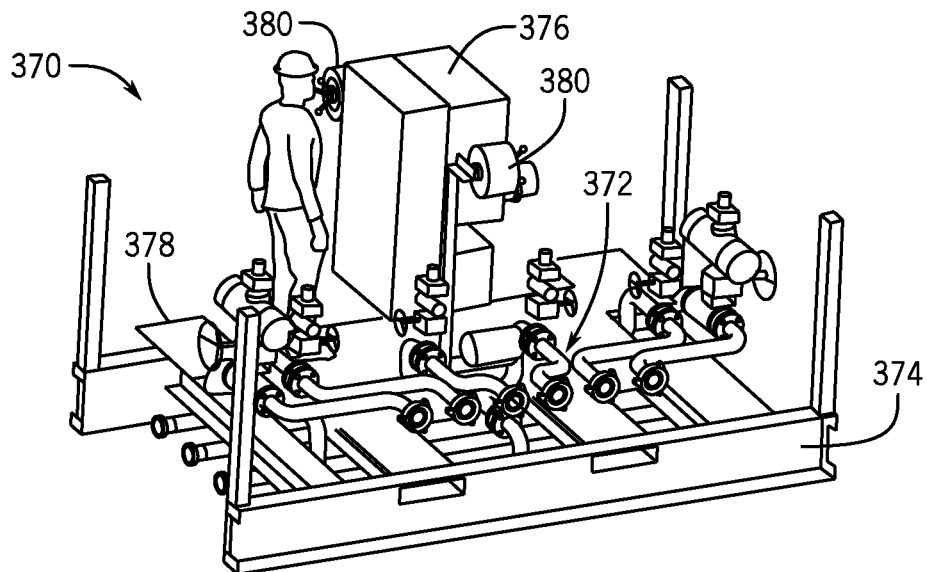
FIG. 16 depicts a tank manifold skid in accordance with an embodiment of the disclosure.

An implementation 370 of a tank manifold skid 286 or 288 is depicted in FIG. 16 as one example. Although just one skid is depicted in FIG. 16, it will be appreciated that the other tank manifold skids deployed in a well testing installation may be identical to the presently depicted implementation 370. The skid is shown in FIG. 16 as having pipework 372 mounted on a platform 374. This pipework 372 and valves for controlling flow through the pipework are discussed in greater detail below with respect to FIG. 17. Like the platform 362, the platform 374 includes slots to facilitate transport and handling of the tank manifold skid. And like the pump manifold skid implementation of FIG. 15, this implementation of the tank manifold skid is also designed for offshore installations per the offshore standard DNVGL-OS-E101 noted above. Power distribution and communication components, such as for facilitating remote actuation of the valves of the tank manifold skid, may be enclosed in an electrical box 376 or in some other suitable enclosure. As shown in FIG. 16, a portion of the pipework 372 can be mounted on the tank manifold skid below decking 378 to facilitate operator movement and reduce tripping hazards on the skid. Various cables and accessories for the control system may be pre-installed on each tank manifold skid before connecting the tank manifold skid to other components. Cables with connectors, which may be reeled from cable reels 380, can be used to make power and control connections with the pump manifold skid for easy offshore installation.

Figure 17:
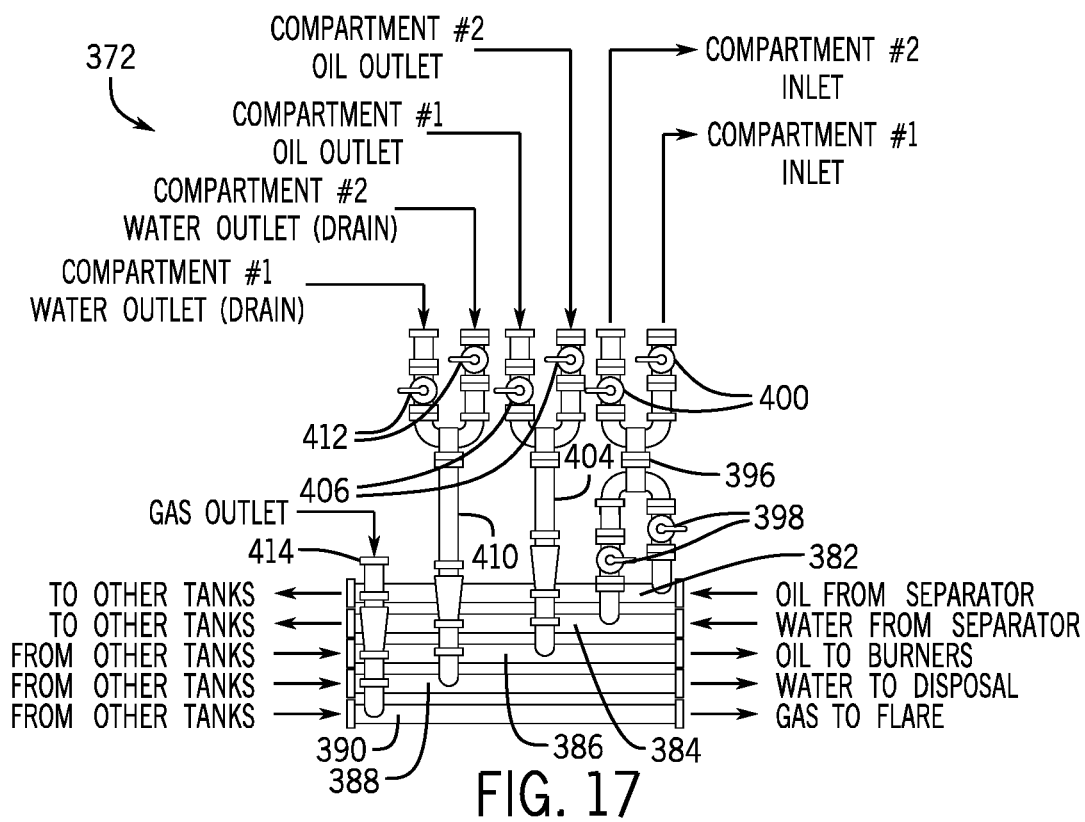
FIG. 17 is a schematic representation of pipework of the tank manifold skid of FIG. 16 in accordance with an embodiment of the disclosure.

A schematic representation of the valves and pipework 372 of the tank manifold skid implementation 370 is depicted in FIG. 17 in accordance with one embodiment. In this example, the pipework 372 enables control of the inlet and outlet of liquids from a two-compartment tank. As shown in FIG. 17, the depicted pipework 372 includes first pipework having pipes 382, 384, 386, 388, and 390. In an installation with multiple fluid tanks and associated tank manifold skids, the first pipework of one tank manifold skid can be coupled to the first pipework of one or more other tank manifold skids. This allows the first pipework of the multiple skids to cooperate and enable fluid communication between the multiple tank manifold skids through the first pipework. For example, the pipes 382 of two or more tank manifold skids may be coupled together to form a trunk line for routing oil from the separator 170 to the tanks. Similarly, the pipes 384 of multiple tank manifold skids may be coupled together to form a trunk line for routing water from the separator 170 to the tanks. The pipes 386, 388, and 390 of each tank manifold skid may be coupled together with the pipes 386, 388, and 390 to form trunk lines for routing oil, water, and gas, respectively, away from the tanks for disposal.

The pipework 372 also includes second pipework having pipes 396, 404, 410, and 414. These pipes of the second pipework function as branch lines that enable fluid communication between the trunk lines embodied by the first pipework and a tank connected to the tank manifold skid. Valves 398, 400, 406, and 412 can be operated to control flow of oil and water between the trunk lines (of pipes 382, 384, 386, and 388) and compartments of the connected tank. In at least some embodiments, the valves on the tank manifold skid are pneumatically actuated and can be remotely operated using a control system, such as that described above. For example, the valves 398, 400, 406, and 412 can be remotely operated from the control panel 368 on the pump manifold skid, from a lab cabin (e.g., via computer system 208), or from a mobile device 214. It will be appreciated that a particular tank can be selected for receiving or distributing oil or water by opening a valve on a branch line of the tank manifold skid of the particular tank, while closing the identical valves of the branch lines of the other tank manifold skids.

The tank manifold skids provide flexibility to connect a suitable number of tanks in different spatial arrangements to suit rig space constraints. Several possible arrangements of four tanks and associated tank manifold skids with a pump manifold skid are depicted in FIGS. 18-20, but in other instances the depicted components can be arranged in some other suitable manner. Further, it will be appreciated that a well testing installation could include some other number of tanks and associated tank manifold skids in still other arrangements.

As generally shown in FIG. 18, an arrangement 420 includes a pump manifold skid 422 with tank manifold skids 424 connected in series, with the tank manifold skids 424 positioned in-line with one another in a single row. Each tank manifold skid 424 is connected to its associated tank 426, and fluids may be routed between the tanks 426 and the pump manifold skid 422 via the tank manifold skids 424, as discussed above. The pump manifold skid 422, the tank manifold skids 424, and the tanks 426 can take any suitable forms, such as the forms described above.

In arrangement 430 of FIG. 19, the tank manifold skids 424 and the tanks 426 are provided in a rectangular arrangement. In this depicted embodiment, the tank manifold skids 424 are provided along outer edges of the arrangement and are connected in series with one another. Piping 432 is provided to connect the tank manifold skids 424 on the left in FIG. 19 with those on the right. FIG. 20 also depicts a rectangular arrangement 440 of tank manifold skids 424 and tanks 426, but with the tanks 426 (rather than the tank manifold skids 424) provided on outer edges of the arrangement. In this embodiment, the tank manifold skids 424 are connected in series, with piping 442 joining the tank manifold skids on the left with those on the right. A walkway 444 can be provided between the tank manifold skids 424 to facilitate operator access to equipment on these skids.

For ease of installation of the well testing apparatus at a wellsite (e.g., on an offshore rig), in some instances a modular portion of the well testing apparatus can be assembled at a non-wellsite location, such as in a remote onshore facility. The assembled modular portion may be transported as a single unit from that non-wellsite location to the wellsite and then connected to additional components as part of the well testing apparatus. In some embodiments, assembling the modular portion of the well testing apparatus at the non-wellsite location can include coupling surge tanks (e.g., tanks 290 and 292) to their respective tank manifold skids (e.g., tank manifold skids 286 and 288) and also coupling those tank manifold skids together so that the surge tanks and their tank manifold skids are connected together as a single unit. This single unit could then be transported to an offshore rig or other wellsite for installation as part of a well testing apparatus.

In other embodiments, assembling the modular portion at the non-wellsite location may include coupling three or more tank manifold skids and tanks to one another as a single unit, or coupling a pump manifold skid with multiple tanks and tank manifold skids as a single unit. In another embodiment, assembling the modular portion of the well testing apparatus at the non-wellsite location can include assembling a part of the modular portion at a first non-wellsite location and assembling another part of the modular portion at a second non-wellsite location. And in at least some instances, any of the modular portions above (including its assembled components and their connections) can be pre-certified (e.g., as assembled in accordance with Det Norske Veritas (DNV) standard for certification No. 2.7-3 (May 2011)) for transport as a single unit.

The foregoing outlines features of several embodiments so that those skilled in the art may better understand aspects of the present disclosure. Those skilled in the art should appreciate that they may readily use the present disclosure as a basis for designing or modifying other processes and structures for carrying out the same purposes or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The invention claimed is:

1. A well testing apparatus comprising:
multiple tanks for receiving fluids;
multiple tank manifold skids connected to the multiple tanks, wherein each of the tank manifold skids includes:
a platform;
first pipework that is mounted on the platform and cooperates with the first pipework of another tank manifold skid to enable fluid communication between the tank manifold skids via the first pipework;

second pipework that is mounted on the platform and enables fluid communication between the first pipework of the tank manifold skid and a tank, of the multiple tanks, that is connected to the tank manifold skid; and valves mounted on the platform for controlling flow of fluids through the second pipework to the tank that is connected to the tank manifold skid;

a pump manifold skid coupled in fluid communication with the multiple tank manifold skids, the pump manifold skid including:

an additional platform;

fluid manifolds mounted on the additional platform;

fluid transfer pumps mounted on the additional platform; and valves mounted on the additional platform for controlling flow of the fluids between the multiple tank manifold skids and the fluid manifolds mounted on the additional platform; and a control system including the valves mounted on the platform, the valves mounted on the additional platform, and a control unit, wherein the control system is configured to permit the control unit to remotely actuate the valves mounted on the platform and the valves mounted on the additional platform via the control unit so as to selectively control flow of the fluids from a separator to the multiple tanks via the pump manifold skid and the multiple tank manifold skids, wherein the control unit is mounted on the additional platform of the pump manifold skid and wherein the pump manifold skid include cables to be connected to the multiple tank manifold skids so as to enable communication of control signals from the control unit to the valves mounted on the multiple manifold skids.

2. The well testing apparatus of claim 1, wherein the fluid manifolds of the pump manifold skid include an oil manifold, a water manifold, and a gas manifold each mounted on the additional platform.

3. The well testing apparatus of claim 1, wherein the fluid transfer pumps of the pump manifold skid include an oil transfer pump and a water transfer pump each mounted on the additional platform.

4. The well testing apparatus of claim 1, wherein the multiple tank manifold skids are connected to the multiple tanks in a one-to-one ratio.

5. The well testing apparatus of claim 1, wherein the multiple tank manifold skids are connected in series with one another.

6. The well testing apparatus of claim 1, wherein the multiple tank manifold skids are coupled together in a single row.

7. The well testing apparatus of claim 1, wherein the multiple tank manifold skids include a first tank manifold skid and a second tank manifold skid that are connected in-line with one another, and a third tank manifold skid that is not connected in-line with the first and second tank manifold skids.

8. The well testing apparatus of claim 1, wherein a human-machine interface for the control unit is mounted on the additional platform of the pump manifold skid.

9. The well testing apparatus of claim 1, comprising a human-machine interface for the control unit, wherein the human-machine interface is provided as a mobile device that is configured to facilitate remote actuation of the valves mounted on the platform and of the valves mounted on the additional platform via the mobile device.

* * * * *